(12) United States Patent
Stoy (10) Patent No.: US 10,555,806 B2
(45) Date of Patent: Feb. 11, 2020

(54) METHOD AND DEVICE FOR OPTIMIZING VISION VIA CUSTOMIZATION OF SPHERICAL ABERRATION OF EYE

(71) Applicant: Medicem Ophthalmic (CY) Limited, Limassol (CY)

(72) Inventor: Vladimír Stoy, Tuchomerice (CZ)

(73) Assignee: Medicem Institute s.r.o, Kamenne Zehrovice (CZ)

( * ) Notice: Subject to any disclaimer, the term of this patent is extended or adjusted under 35 U.S.C. 154(b) by 74 days.

(21) Appl. No.: 15/571,185

(22) PCT Filed: May 2, 2016

(86) PCT No.: PCT/IB2016/052487
§ 371 (c)(1),
(2) Date: Nov. 1, 2017

(87) PCT Pub. No.: WO2016/178133
PCT Pub. Date: Nov. 10, 2016

(65) Prior Publication Data
US 2018/0344451 A1 Dec. 6, 2018

Related U.S. Application Data

(60) Provisional application No. 62/155,674, filed on May 1, 2015.

(51) Int. Cl.
*A61F 2/16* (2006.01)
*A61F 2/14* (2006.01)
(Continued)

(52) U.S. Cl.
CPC .............. *A61F 2/164* (2015.04); *A61B 3/103* (2013.01); *A61B 34/10* (2016.02); *A61F 2/1451* (2015.04); *A61F 2/1605* (2015.04); *A61F 2/1624* (2013.01); *A61L 27/52* (2013.01); *A61B 2034/108* (2016.02); *A61B 2503/06* (2013.01); *A61F 2/1627* (2013.01);
(Continued)

(58) Field of Classification Search
CPC .... A61F 2/1624; A61F 2/1627; A61F 2/1635; A61F 2/1613; A61F 2/1637; A61F 2/164; A61F 2002/16965; A61F 2230/0078; A61F 2210/0014; A61F 2/1659
See application file for complete search history.

(56) References Cited

U.S. PATENT DOCUMENTS

| 5,674,283 A | 10/1997 | Stoy |
| 9,155,614 B2 | 10/2015 | Blum et al. |

FOREIGN PATENT DOCUMENTS

| CN | 102411220 A | 4/2012 |
| GB | 2151371 A | 7/1985 |

(Continued)

*Primary Examiner* — David H Willse
*Assistant Examiner* — Javier G Blanco
(74) *Attorney, Agent, or Firm* — Fox Rothschild LLP (57) ABSTRACT

Artificial lenses and methods for optimizing vision in an eye of a patient comprising the steps of determining a target optical configuration including the optimum defocus and aberrations that the patients' eye should have in order to match or approximate the original optical configuration of the patient; determining the refractive change of the patient's eye required to achieve the optical configuration best corresponding to target optical configuration for the patient; and implementing the selected refractive change to achieve the target optical configuration.

7 Claims, 7 Drawing Sheets

(51) Int. Cl.
*A61B 34/10* (2016.01)
*A61B 3/103* (2006.01)
*A61L 27/52* (2006.01)
*G02C 7/02* (2006.01)

(52) U.S. Cl.
CPC ... *A61F 2/1635* (2013.01); *A61F 2002/16965* (2015.04); *A61F 2210/0014* (2013.01); *A61F 2230/0078* (2013.01); *G02C 7/027* (2013.01)

(56) References Cited

FOREIGN PATENT DOCUMENTS

| WO | 00008516 A1 | 2/2000 |
| WO | 060060971 A1 | 6/2006 |
| WO | 14111769 A1 | 7/2014 |

METHOD AND DEVICE FOR OPTIMIZING VISION VIA CUSTOMIZATION OF SPHERICAL ABERRATION OF EYE

This application claims the benefit of U.S. Provisional Application No. 62/155,674, filed on May 1, 2015, the contents of which are incorporated herein by reference.

FIELD OF THE INVENTION

This invention relates to a method for presbyopia treatment and vision optimization via customization of spherical aberration of eye. It also relates to devices that facilitate such customization.

BACKGROUND OF THE INVENTION

There is a long-term quest in ophthalmic surgery to improve human vision by improving optical quality of the eye. It is usually taken for granted that the eye is just another optical instrument, and that perfect vision requires a perfect projection of the image on the retina. To achieve this goal, all optical elements of the eye (primarily the cornea and the lens) are believed to be as aberration-free as possible and should be combined to form an aberration-free imaging system. It is generally assumed that any aberration will degrade visual acuity and decrease contrast sensitivity, in addition to potentially creating other visual disturbances, such as glare and halos in certain situations.

Spherical aberrations in human population have been the subject of study. Optical components even in a young, healthy eye may have significant aberrations, but they are deemed to largely compensate each other in a young, healthy eye. Since the spherical aberration of the eye is generally deemed to be detrimental to the vision quality, optical aberrations of patient's cornea, particularly spherical aberrations, are sometimes corrected by implantation of an aspheric intraocular lens ("IOL") with opposite spherical aberration.

Consequently, there are numerous patents and patent applications covering methods and devices for decreasing aberrations of the eye, such as the following: Norrby, Sverker et al: Methods Of Obtaining Ophthalmic Lenses Providing The Eye With Reduced Aberrations, US Patent Application Publication No. 20020105617; Tabernero, Juan et al: Intraocular Lens For Correcting Corneal Coma, US Patent Application Publication No. 20070093891; Norrby, Sverker et al: Methods Of Obtaining Ophthalmic Lenses Providing The Eye With Reduced Aberrations, US Patent Application Publication Nos. 20040088050; 20070121064; 20070258044; 20090036980; 20110082542 and 20120059463; Lai; Shui T.: Intrastromal Surgery Correcting Low Order And High Order Aberrations Of The Eye, US Patent Application Publication No. 20080039825; Weeber; Hendrik Albert, et al.: System, Ophthalmic Lens, And Method For Extending Depth Of Focus, US Patent Application Publication Nos. 20090210054 and 20130060330; Portnoy, V.: Adjustable Multifocal Intraocular Lens System, U.S. Pat. No. 8,287,593; and Marmo, J. C.: Corneal Onlays And Wavefront Aberration Correction To Enhance Vision, U.S. Pat. No. 7,585,075, each of which is incorporated herein by reference.

Some investigators also describe post-operative adjustment of either optical aberrations of the cornea or the implanted artificial lens, particularly their spherical aberration ("SA") of the lens in order to decrease the overall aberration of the eye. This is usually achieved by introducing a controlled degree of asphericity that also, in addition to causing certain amount of SA, also increases the depth of focus of the lens. Such methods and devices are described in numerous patents and patent applications, such as: Sandstedt; Christian A., et al.: Using The Light Adjustable Lens (LAL) To Increase The Depth Of Focus By Inducing Targeted Amounts Of Asphericity, US Patent Application Publication No. 20130072591; Peyman, Gholam A.: Intrastromal Corneal Modification Via Laser, US Patent Application Publication No. 20010027314; Adjustable Ablatable Inlay, US Patent Applications Publication Nos. 0020138069 and 20020138070; and Ablatable Intracorneal Inlay With Predetermined Refractive Properties, US Patent Application Publication No. 20030093066; Smith, David J., et al.: Accommodating Intraocular Lens System Having Spherical Aberration Compensation And Method, U.S. Pat. No. 7,637,947; and McGinn J. T., et al.: Electro-Optic Lenses For Correction Of Higher Order Aberrations, U.S. Pat. No. 8,154,804, each of which are incorporated herein by reference.

Some inventors describe intraocular lenses that change optical properties by transfer of fluid within its optics, and can be potentially used even for adjustment of SA, although that goal is usually not explicitly stated. Such inventions are described e.g. in the following US patent applications and granted US patents: Shadduck, John H.: Adaptive Optic Lens And Method Of Making, US Patent Applications Publication Nos. 20040184158; 20060061729; 20070299487; 20130060331; and Intraocular Implant Devices, U.S. Pat. No. 8,048,155; Sacharoff; Alex, et al.: Non-Invasive Power Adjustable Intraocular Lens, US Patent Application Publication No. 20090281620; Shadduck, John H.: Adaptive Optic Lens And Method Of Making, U.S. Pat. No. 7,264,351; Shadduck, John H.: Adaptive Optic Lens System And Method Of Use, U.S. Pat. No. 7,278,739; Esch, Victor: Lens System And Method For Power Adjustment Using Externally Actuated Micropumps, U.S. Pat. No. 7,438,723; Esch, Victor: Methods Of Adjusting The Power Of An Intraocular Lens, U.S. Pat. No. 7,485,144; DeBoer, et al.: Accommodating Intraocular Lens, U.S. Pat. No. 8,715,345; Phillips, A. Accommodating Intraocular Lens, U.S. Pat. Nos. 7,601,169 and 8,500,806; Boyd, et al.: Intraocular Accommodating Lens And Method Of Use, U.S. Pat. No. 8,167,941; Sean McCafferty, Accommodating Fluidic IOL With Flexible Interior Membrane, US Patent Application Publication No. 20140257478 and Refocusable Intraocular Lens With Flexible Aspheric Surface US Patent Application Publication No. 20140257479, each of which are incorporated herein by reference.

Change of the optical properties of the natural (e.g., human cornea) or an artificial lens by changing refractive index of their material are also described in numerous papers, patents and patent applications, such as: Phillips, A. J., System and Method for Treatment of Hyperopia and Myopia, U.S. Pat. No. 6,102,906, Bille J. F.: System For Forming And Modifying Lenses And Lenses Formed Thereby, U.S. Pat. Nos. 8,292,952; 8,920,690; 9,192,292; Sahler; Ruth et al.: "Hydrophilicity alteration system and method" U.S. Pat. Nos. 9,023,257; 9,186,242 and 9,107,746; Sahler; Ruth et al.: "intraocular lens (IOL) fabrication system and method" US Patent Application Publication No. 20160074967; Smith, T. et al.: Optical Hydrogel Material With Photosensitizer And Method For Modifying The Refractive Index, US Patent Application Publication Nos. 20130268072; 20090287306 and U.S. Pat. No. 8,901,190; Knox, Wayne H. et al.: Optical Material And Method For Modifying The Refractive Index, U.S. Pat. Nos. 8,932,352;

8,337,553; 7,789,910 B2; Knox, Wayne H. et al.: Optical Material And Method For Modifying The Refractive Index, US Patent Applications Publication Nos. 20130138093; 20130178934; 20100298933; 20080001320; 20090143858; 20090143858; Knox, Wayne H. et al.: Method For Modifying The Refractive Index Of An Optical Material And Resulting Optical Vision Component, US Patent Application Publication No. 20120310340, Knox, Wayne H. et al.: Method For Modifying Refractive Index Of Ocular Tissues, U.S. Pat. Nos. 8,486,055; 8,512,320; 8,617,147 and US Patent Application Publication Nos. 20110071509; 20130226162 and 20140107632; Knox, Wayne H. et al.: Method For Modifying Refractive Index Of Ocular Tissues And Applications Thereof, US Patent Application Publication No. 20120310223, each of which is incorporated herein by reference.

Spherical aberration can be also changed by implantation of an aspheric lens with conic optical surfaces, such as those described in the following patents and patent applications: Stoy, V. et al.: Bioanalogic Intraocular Lens, International Patent Application Publication No. WO2014111769; Wichterle, O.: Method Of Molding An Intraocular Lens, U.S. Pat. No. 4,846,832; Wichterle, O.: Soft And Elastic Intracameral Lens And Method For Manufacturing Thereof, U.S. Pat. No. 4,846,832; Stoy, V.: Implantable Ophthalmic Lens, A Method Of Manufacturing Same And A Mold For Carrying Out Said Method, U.S. Pat. No. 5,674,283; Sulc, J., et al.: Soft Intracameral Lens, U.S. Pat. Nos. 4,994,083 and 4,955,903; Blake, et al.: Aspheric soft lens, U.S. Pat. No. 7,192,444; Blake, et al.: Method Of Making Aspheric Soft Lens, U.S. Pat. No. 6,007,747; Hong, et al.: Intraocular Lens, U.S. Pat. No. 7,350,916; Hong, et al.: Aspheric Toric Intraocular Lens, U.S. Pat. No. 8,167,940; Hong, et al.: Optimal Intraocular Lens Shape Factor For Human Eyes, US Patent Application No. 20060227286; Portnoy, A.: Contra-Aspheric Toric Ophthalmic Lens, U.S. Pat. No. 8,668,333; and Michalek, J. et al.: Method Of Manufacturing An Implantable Intraocular Planar/Convex, Biconvex, Planar/Concave Or Convex/Concave Lens And A Lens Made Using This Method, U.S. Pat. No. 8,409,481, each of which is incorporated herein by reference.

The relation between the optical parameters of the eye and visual perception has been widely studied. The results show that individual optical components have significant aberrations, but they are deemed to largely compensate each other in a young, healthy eye. However, much of this relation is hitherto unexplained satisfactorily.

SUMMARY OF THE INVENTION

This invention relates to a novel method for presbyopia treatment and vision optimization via customization of spherical aberration of eye and to a device that facilitates such customization.

One aspect of this invention discloses a method of optimizing vision in an eye of a patient. The method comprises the steps of: (i) determining a target optical configuration ("TOC"), including, e.g., optimum defocus and aberrations, that the patient's eye should have in order to match or approximate an original optical configuration ("OOC") of the patient; (ii) determining a refractive change of the patient's eye required to achieve the optical configuration best corresponding to the TOC for the patient; and (iii) implementing the selected refractive change to achieve the TOC.

The target and original optical configurations of the eye can be determined using a number of methods. For example, the optimum defocus and aberrations can be determined to arrive at the TOC. The TOC corresponds to the configuration the patients' eye should have in order to match the optical parameters that the individual had in his/her younger years when his/her eyesight was at their best, i.e. the original optical configuration. The OOC determination can be achieved by various methods.

In one example, the OOC is an optical configuration of the patient at a young age when he or she had good eyesight. In that case, the OOC determination involves performing a thorough eye examination of the young patient with good eyesight, calculating eye's optical parameters including aberrations, refractive indices and geometry of cornea, lens, vitreous body, retina, fovea and sclera, and storing such data; then in the case need (e.g., presbyopia, cataract, etc.), retrieving the stored data, determining the OOC, making any necessary adjustments for changes in eye properties (size, retinal corneal or lens geometry, refractive indices, etc.); and calculating the corresponding optical eye parameters, e.g. aberrations, needed to recalculate OOC into TOC.

In another example, the OOC can be determined by a process involving performing a thorough eye examination of the candidate patient to determine the relevant eye parameters, extrapolating the relevant data back to the time when the eyesight of that individual was satisfactory, and calculating or estimating the original OOC and then TOC assuming most likely changes in eye properties over the time interval between the time for which OOC was estimated and time of the expected corrective procedure.

In some embodiments, the thorough eye examination of the patient can include determining geometry of macula and the determining of the target optical configuration includes correction on the macular geometry.

After the TOC is ascertained, one can then determine the refractive change of the patient's eye (defocus, aberrations) required to achieve the optical configuration best corresponding to TOC for that individual.

The next step involves implementing the selected refractive change to achieve the TOC. Refractive change can be achieved by many methods known in the art. In one example, the TOC can be achieved by refractive changes in cornea by changing its shape and/or refractive index by methods and devices that are known per se to those skilled in the art, such as LASIK, PRK, corneal crosslinking, laser-induced changes of corneal refractive index, change of corneal shape by implantation of solid elements (e.g., INTACTS). In another example, the TOC can be achieved by refractive changes to the crystalline lens, such as of laser lensectomy. Alternatively, the TOC can be achieved by adding lenses (e.g., an artificial lens implant) onto or into cornea, into the anterior chamber of the eye, into the posterior eye chamber between iris and natural lens, or by replacing the natural lens with an artificial IOL. In one embodiment, an example method of refractive change comprises implantation of a customized lens with subsequent fine in situ adjustments of the lens or of the ocular tissues by absorption of electromagnetic energy. An example method of application of the electromagnetic energy involves the use of a laser, particularly femtosecond or attosecond laser. The lens has optical parameters necessary to achieve the target optical configuration of the eye. In some examples, the artificial lens implant has spherical aberration customized to achieve the target optical configuration of the eye. In others, the artificial lens implant has optical parameters adjustable postoperatively and the implementing step comprises a postoperative adjustment of the artificial lens. The postoperative adjustment can be achieved by a controlled absorption of electromagnetic radiation, or by change of shape of one or more memory elements embedded in the lens and said change is achieved by a controlled absorption of electromagnetic radiation, or by a change of the refractive index in selected location of the lens.

Preferably, the artificial lens implant comprises hydrophilic polymer material. The hydrophilic material can be a hydrogel with liquid content of about 17% or more (e.g., 17%, 18%, 19%, 20%, 25%, 30%, 35%, 40%, 45%, 50%, 60%, 70%, 80%, or 90%) by weight in equilibrium with intraocular environment. In some examples, the hydrophilic material is a hydrogel with liquid content between about 40% and 50% (e.g., 40%, 41%, 42%, 43%, 44%, 45%, 46%, 47%, 48%, 49% or 50%)) by weight in equilibrium with intraocular environment. The hydrophilic material or hydrogel can comprise a polymer containing a minor part of monomer units with pendant carboxylic group, such as a polymer containing a minor part of monomer units with pendant groups capable of absorption of UV radiation.

Accordingly, another aspect of this invention provides a device, such as an artificial lens implant, for carrying out the above-described methods.

In one embodiment, this invention discloses an artificial lens, implantable into a human eye that includes an optical component having a central anterior optical surface within a first boundary and defining an anterior apex and a central posterior optical surface within a second boundary and defining a posterior apex. The optical axis connects the anterior and posterior apexes. Memory elements can be embedded in the lens for shaping the optical surfaces of the lens. The anterior and posterior optical surfaces are defined by a rotation of one or more aconic sections defined by a function of the distance from the posterior or anterior apex. The aconic function is selected to provide a target optical configuration that conforms to an original optical configuration of the eye. An example of the device for performing the refractive change is an implantable lens whose optical properties can be modified by absorption of electromagnetic energy either before or after the lens implantation. The modification of the optical properties can be achieved either by changing the refractive index of a material comprising the lens, or by changing the shape of memory elements embedded within the lens. Example memory elements are made from a shape memory polymer with at least one transition temperature higher than 40° C.

A preferred device for such of correction is an artificial lens, implantable into a human eye, that includes an optical component having an optical axis, ananterior optical surface with an anterior apex and a posterior optical surface a posterior apex. Optionally, such lens may comprise embedded in the lens memory elements for shaping the optical surfaces of the lens, such elements being advantageously activated by absorption of electromagnetic energy to the lens geometry. At least one of the anterior and posterior optical surfaces is a conic surface defined by a rotation of one or more conic sections. More preferably, multiple conic surface can be replace by a single aconic surface defined by rotation of a curve defined by a function used to describe a conic curve in which at least one of the "Central radius" (or its reciprocal called Curvature) and the "Conic constant" are function of the distance from the optical axis. The conic section parameters or aconic function are selected to provide a target optical configuration that conforms to an original optical configuration of the eye.

Another preferred device for achieving the TOC is a hydrogel implant into the eye which refractive index can be changed by absorption of electromagnetic energy. The same end can be achieved by changing refractive index of the natural crystalline lens (NCL) of cornea by absorption of electromagnetic energy.

The resulting lens and/or cornea would not be necessarily optically perfect in the usual sense of that term by themselves or in their combination, on the contrary, they should be optically imperfect in their combination to approximate optical aberrations as the young eye of that particular patient.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

This invention is based, at least in part, on an unexpected finding that quality vision of an eye is not solely determined by optics of the lens. Rather, each eye has developed its individual geometry, optical properties of the lens, and neural system to achieve the optimum vision. Any aberration of the lens is particularly related to the individual geometry of macula. Therefore, each individual lens has an optimum specific spherical aberration corresponding to the aspherical aberration of the lens at the time the eye was fully developed but still young.

For example, even eyes of a young, healthy person with very good visual quality are not perfect optical systems and have rather variable value of SA. SA is the value expressing the change of the focal length with the distance of the incoming ray from the main optical axis. It can be positive or negative, and it is expressed usually in microns as the value of the coefficient W4 in the Zernike polynomial. SA of the eye is a result of combined contributions of SA values of all optical elements of the eye, primarily of the cornea and of the lens. Each element contributes to the SA by its anterior and posterior side (from the viewpoint of the incoming light). SA of the cornea is usually positive and rather constant over the lifetime. On the other hand, SA of even a young, healthy human lens can be either positive or negative and its absolute value increases generally with age; and consequently, the SA of the whole eye increases with age and can be positive or negative at any age, including the young age.

The expectation derived from conventional optical theory is that high SA values (positive or negative) should make the vision blurry and should degrade the Contrast Sensitivity (CS), particularly at poor (so called mezopic) light conditions. While studying clinical results in patients with our proprietary polyfocal lenses having highly negative SA values, it was noted that parameters related to visual quality, such as visual acuity (VA) and CS, are very good regardless the highly negative SA value of the implanted lens, and essentially independent on its SA value. This is contrary to the expectation derived from conventional optical theory. These surprising results seem to be in agreement with the fact that the SA values are highly variable even for young, healthy eyes with nearly perfect vision. A large part of young subjects may have lenses and eyes with high negative aberration. This proportion decreases with age, and the average SA value grows with age toward more positive values while the vision quality conceivably decreases.

The high negative SA value of the natural crystalline lens (NCL) is a consequence of two structural features of NCL: approximately hyperboloid shape of the NCL on both posterior and anterior side leads to its polyfocality, i.e. decrease of its local refractive power with the distance from the optical axis. (This type of polyfocality corresponds to a negative SA value). Hyperboloid-type shape of the lens, and thus the negative SA value, increases with increasing negative value of so called conic constant k.

The posterior side of younger subjects is hyperboloid with negative value of conic constant, which becomes more negative with accommodation stimulus. This shows that the studied relatively young lenses have negative SA and values are getting even more negative if the subject attempts to see to near.

Figure 1A:
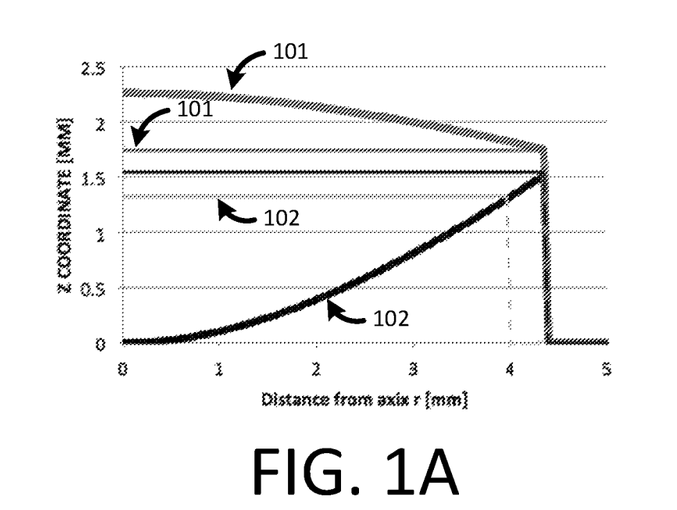
FIG. 1A is a diagram of a half-profile of a lens defined by anterior and posterior surfaces and exemplifying also the geometry of a NCL.
Figure 1B:
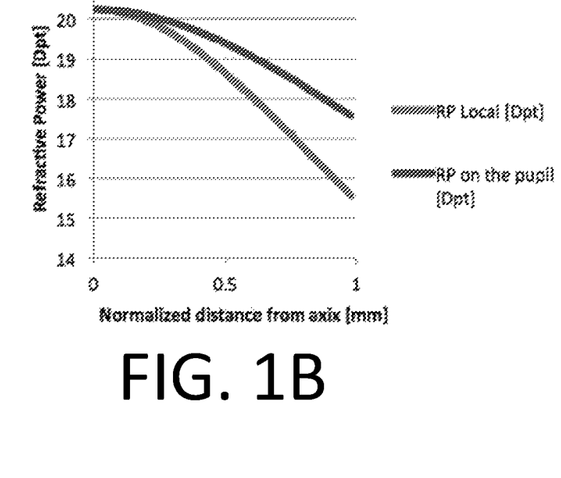
FIG. 1B is graph showing local refractive power as a function of distance from a central axis and exemplifying also the geometry of a NCL or an implant with negative SA.
Figure 2:
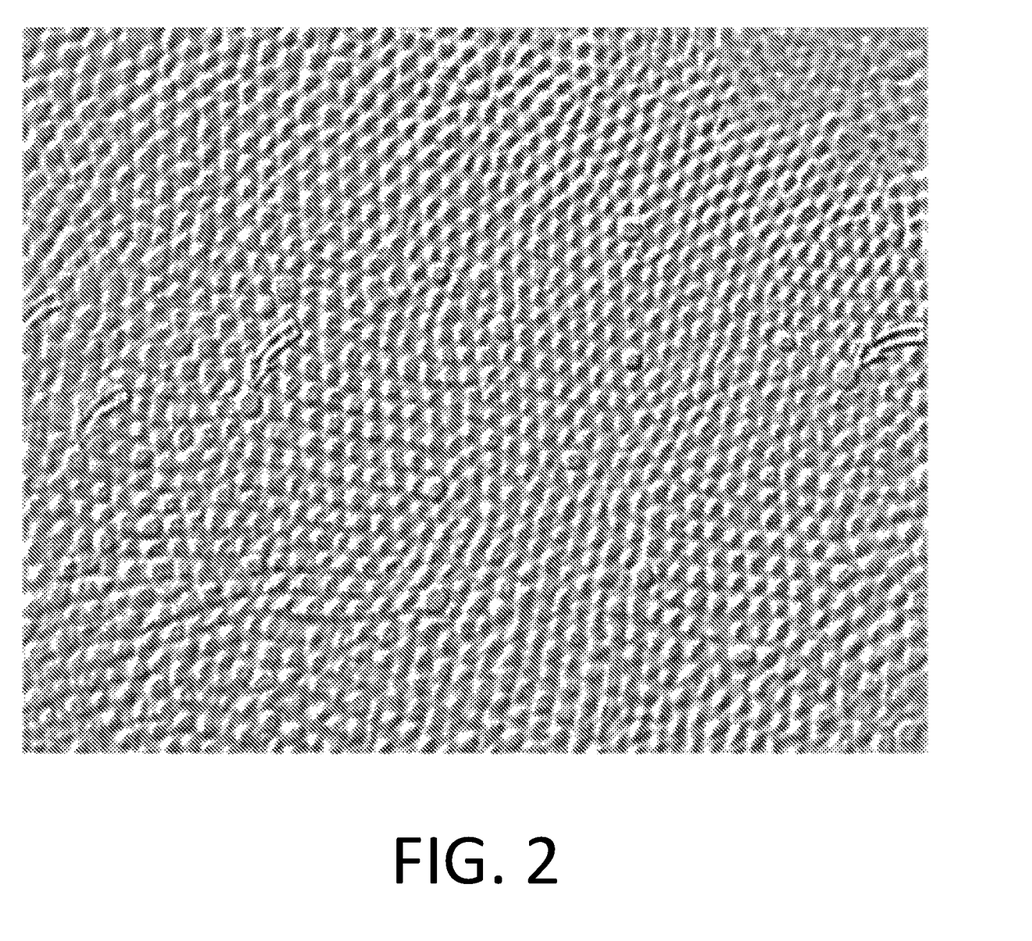
FIG. 2 is an optical coherence tomography image of macula with a layer of densely packed photo receptors.

Referring to FIG. 1A, a half-profile of a lens is shown defined by anterior 101 and posterior 102 surfaces with different negative conic constants $k_a$ and $k_p$ for the anterior 101 and posterior 102 surfaces, respectively. In an example shown in FIG. 1A, the calculated geometrical and optical profiles for a 20.5 diopter NCL are $k_a=-11$ and $k_p=-2$. The k-values used here can be selected from values for human lens found in some references. The local refractive power decreases with distance from the axis, and refractive power of the lens also decreases with pupil diameter, as shown in FIG. 1B.

It has also been shown that while the NCL is hyperbolic with negative aberration in young persons, it becomes spherical with positive SA in older age.

The hyperbolic shape of NCL, particularly in younger eyes and under accommodation, was also confirmed by a different imaging method (MRI studies) in live patients.

The gradient of refractive index (GRIN) in the NCL provides additional polyfocality to NCL and increases the negative SA value particularly in a young NCL. GRIN vanishes with age by even a greater rate than the hyperbolic shape.

Young NCL has GRIN that makes SA even more negative than the hyperbolic lens geometry with negative k-value. GRIN (as well as hyperbolicity) decreases with age as the NCL becomes more optically homogenous as well as more spherical. A major part of polyfocality is contributed by GRIN and a minor part by hyperboloid surfaces.

All this evidence shows that the human eye is a rather imperfect optical instrument, particularly its NCL and particularly a young NCL. This can be shown also e.g. by low values of the Modulus Transfer Function (MTF) in normal healthy eyes by measuring MTF functions of a normal NCL in vivo.

Young lenses are apparently providing high quality vision regardless of their low optical quality as measured by the MTF function. The following disclosure discusses the explanation for this dilemma.

Visual correction has made considerable progress in the last 50 years or so. For each refractive problem, there are numerous options of correction that are suitable for various situations, indications, ages and personal preferences: contact lenses, LASIK, phakic ICI or anterior chamber lenses, intrastromal implants, IOLs of various designs, corneal crosslinking, and other.

However, these technologies could give us vision quality no better than vision provided by our young, healthful eyes. "Vision quality" is a complex affair that is only partly reflected by ophthalmologist's tests: accommodation from very near to infinity under any light conditions, depth of perception, contrast sensitivity, peripheral vision, night vision, instantaneous refocusing, color perception, distance awareness, pattern recognition, dealing with glare and sudden changes of illumination, and other aspects useful in our daily lives. All these capabilities may be very natural and effortless for humans in younger years, but once gone, that can only be partly recovered by modern ophthalmic technologies.

Part of the reason is that quality vision is not solely determined by excellent optics of the lens. As shown above, natural crystalline lenses are not very good lenses in the general optical sense: some of them have very high spherical aberration, particularly in our younger years when our vision quality was at its best. And natural lenses are not only optically imperfect, but also highly variable even from one young healthy person to another.

The fact that we could see very well through the lens that is optically inferior strongly indicates a somewhat weak connection between optical quality and visual quality in a healthy human eye. Simply speaking, a healthy young eye is a perfect imaging system of imperfect optical quality.

The eye compensates the "poor" optical quality (by the usual optical standards) of the lens in at least two ways. First, at least part of this contradiction can be probably explained by the processing power of the brain ("neural adaptation"). For example, an image projected on our retina is converted into a certain signal pattern generated and pre-processed by retinal cells, to be transferred via the optical nerve to our brain. This pre-processing is demonstrated by the presence of many more photosensitive cells in the retina than optical fibers transferring the signal from the retina to visual cortex. This processed signal pattern is then interpreted in our visual cortex as a certain visual image that we perceive. What a person "sees" then is the visual image generated by his/her brain, not the optical image projected by the lens on retina. Apparently, retina and brain processing in each person has developed together with the individual lens to provide the "good vision" optimum for that person's "survival", no matter how his/her particular lens deviates from a "perfect lens" from viewpoint of optical physics. Each human, then, has a "customized" visual system composed from optics (eye) and processing unit (retina and brain) that co-developed over time after birth.

Another part of this contradiction conceivably results from the anatomy and geometry of the retina in general and fovea in particular. Lenses are characterized by their ability to project a picture of separate points from the object (i.e., from an "object plane") as separate points on the "image plane". If the lens is optically imperfect with low MTF or high Spherical (or other) aberration, then image of the of the object projected into the image plane is blurred, i.e. close though separate points on the object become fused and indistinguishable in the image plane. However, image of the same object is projected by an aberration-free lens on a concave surface, for example, rather than on a plane, it would become blurred in a similar way as the image projected on a plane by a lens with positive SA. By the same token, the image projected through an aberration-free lens on a convex surface would be blurred similarly as an image projected by a lens with negative SA on a plane. Thus, for each lens with certain aberration there is one and only one surface geometry on which the image is projected with the best resolution (e.g., plane for an aberration-free lens, concave for lens with positive SA, convex with negative SA, cylindrical for astigmatic lens, etc.).

The image in the eye is not projected on some imaginary image plane (which could be represented by a flat film in a camera), but on the "image surface" in the retina, i.e. on the layer of the photoreceptor cells. This "projection surface" is concave with radius of curvature around 12 mm for a greater part of the retina. In the fovea pit, however, where the central vision with the highest resolution is realized, the photoreceptor surface is convex with relatively small apex radius and apparently aspheric with positive SA (as shown in the FIG. 3B).

To complicate the situation some more, the photoreceptor layer is placed behind (from the viewpoint of the incoming light) the several neural and granular layers of retina having the Inner Limiting Membrane (ILM) on its anterior surface. This ILM surface is concave and parallel to the surface of the photoreceptor layer for most of the retinal area, only in the foveal pit area it becomes an apparently aspheric concave surface with a small radius of curvature and perhaps negative SA. This is clearly visible in FIG. 3B showing OCT picture published by Helga Kolb in http://webvision.med.utah.edu/wp-content/uploads/2011/01/OCTmacula.jpg/.

Figure 3:
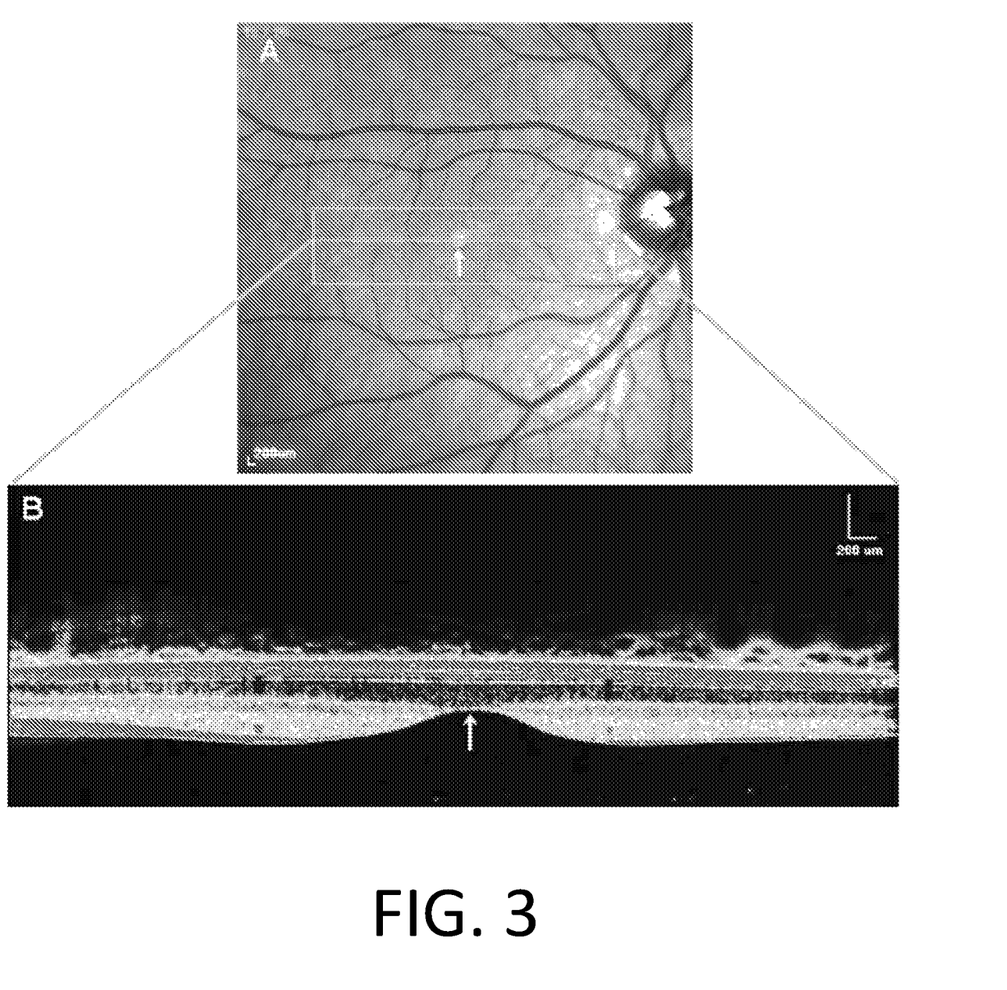
FIG. 3A is a fundus photo of a normal human macula, optic nerve and blood vessels around the fovea.
FIG. 3B is an optical coherence tomography image of profile of the same macula shown in FIG. 3A showing the local convexity of photoreceptor surface in the macula.

In FIG. 3, the portion labeled A) is a fundus photo of a normal human macula, optic nerve and blood vessels around the fovea and the portion labeled B) shows optical coherence tomography (OCT) images of the same normal macula in the area that is boxed in green above (A). The foveal pit (arrow) and the sloping foveal walls with displaced inner retina neurons (green and red cells in the original picture) are clearly seen. Blue cells (in the original picture) are the packed photoreceptors, primarily cones, above the foveal center (pit).

From the viewpoint of the visible light (coming from below in the direction of the arrow denoting the foveal pit center), the retinal surface forms an additional refractive optical interface and the surface of the photoreceptor layer (blue color in the original picture) is the surface on which the image is projected. The consequence of this arrangement is that an aberration-free lens would form a blurred image in the area of the foveal pit where the density of the photoreceptors is the highest since the photoreceptor layer here is formed mainly by rods in the hexagonal arrangement.

Conversely, the eye has to have a specific optical aberration to form a sharp image on fovea of some particular geometry. Since the photoreceptor layer is convex, the eye should have negative SA in the central optical area. This could explain the peculiar profiles of the refractive index gradient in young human lenses, and the fact that the negative aberration caused by the young lens geometry becomes even more negative during the accommodation. From this viewpoint, the "imperfect" optics of the healthy human lens appears to be a functional necessity rather than some sloppiness of nature that is compensated by neural adaptation only.

That could also explain at least partly why implantable lenses with high negative SA are well accepted by patients and provide good visual acuity and high contrast sensitivity.

Since the geometry of retina and fovea are highly individual features, then the lenses will have corresponding individual aberrations to achieve optimum vision quality. From this viewpoint, the SA variability of human lenses appears to be a functional necessity and logical consequence of individual variability of the human eye geometry.

All components involved in the visual perception—the surface defined by the ILM and photoreceptor layer geometry of retina in general and macula and fovea in particular, the lens' refractive profile (its aberrations) and the signal processing patterns/capabilities in the retina/brain system—are mutually customized and optimized with respect to each other as they develop in parallel during the childhood to provide the optimum visual result.

The human eye starts very well, but has one inherent problem. It was originally designed for a considerably shorter "service life" than is the contemporary human lifespan. As it ages, the eye grows in size and develops various optical defects (e.g., corneal defects, tear film disruptions, vitreous body shrinkage, etc.). Significantly, both the eye as a whole and the lens grow continuously with age, changing the eye's optical parameters. Moreover, the lens surfaces change their geometry from their hyperboloid-like shape in young age to spherical in the older years. The refractive index gradient of young lens with its major contribution to its negative SA gradually disappears with age so that lens changes its SA from negative to positive. All this causes decrease in the negative spherical aberration of the lens and increase of the SA of the eye. This could be seen as a favorable development by an optical physicist, but it represents a change in optics that may impose some new challenge to the image-processing neural system residing in retina and visual cortex. In mature age, this change in the SA of the lens probably cannot be compensated by corresponding changes in the geometry of retina and/or fovea. And although our visual system has built-in a considerable flexibility, from some point on the "processing unit" (that's performance does not improve with the age either) cannot adapt anymore to new optical patterns. And consequently, our vision quality deteriorates with age.

The optical deficiency can be partly cured by a refractive change by adding a lens (e.g. glasses), or by changing one of the lenses in the eye (e.g., cornea by LASIK) or by replacing the degraded natural lens for an IOL.

The current ophthalmic science prefers the refractive change that minimizes overall eye aberrations, particularly astigmatism and SA. However, such change will not necessarily achieve the desirable match between the optical profile, retinal/foveal geometry and requirements on the image-processing neural system residing in retina and visual cortex that was originally established during the development since that individual's infancy.

As disclosed herein, an optimum visual result may be achieved by restoring the optical configuration that conforms the retinal geometry and neural patterns of the individual patient that were developed over time and worked for that individual best in his or her younger years. More specifically, the method of optimizing vision in an eye of a patient comprising the following steps: (i) determining a TOC (including optimum defocus and aberrations) that the patient's eye should have in order to match or approximate an OOC of the patient; (ii) determining the refractive change of the patient's eye required to achieve the optical configuration best corresponding to TOC for the patient; and (iii) implementing the selected refractive change to achieve the TOC.

An optimum defocus and aberrations that the patients' eye should have in order to match the optical parameters of that individual had in his/her younger years when his/her eyesight was at their best is determined (i.e., the above-mentioned OOC). OOC involves at least the geometry of cornea, the geometry of the lens, and geometry of retina (including fovea), plus refractive indices (and the refractive index gradients) of all optical media along the optical path. OOC determination can be achieved by one of a number of methods as described below.

For example, the OOC can be based on a patient's past eye examination record. In that case, a thorough eye examination of that patient may have been performed when he or she was young and had good eyesight using any suitable methods known in the art, including e.g., biometry, aberrometry, eye and retinal geometry by OCT and/or MRI and/or Scheimpflug camera and/or ultrasonic microscopy, and/or by some other method that becomes available by the time of eye exam. Based on results from the examination, a clinician can calculate various parameters of each eye, including the optical aberrations, refractive indices and geometry parameters of cornea, lens, vitreous body, retina, fovea and sclera and store such data in his/her medical records. Then, in the case of eye problem later on (presbyopia, cataract, etc.), the stored data can be retrieved and used as the OOC. At this later time, a thorough eye examination of the same patient can be carried out again to obtain a second set of data. The second set data is compared with the OOC. Based on the comparison, a clinician can make any necessary adjustments for changes in eye properties (size, retinal corneal or lens geometry, refractive indices, etc.) found from the new biometry and aberrometry; and calculate the corresponding optical aberrations needed to determine a TOC.

Alternatively, in the case that the OOC was not originally recorded and there is no past eye examination record, a thorough eye examination of the candidate patient may be performed by any suitable methods known in the art, such as e.g., biometry, aberrometry to determine refractive patterns, aberrations, refractive indices, eye, lenticular and retinal geometry by OCT and/or MRI and/or Scheimpflug camera and/or ultrasonic microscopy or by another method known to experts at that time. The relevant data can be extrapolated back to the time when the eyesight of that individual was satisfactory to obtain the OCC estimate. After comparing the relevant data and OCC, a clinician can calculate or estimate the values of relevant data (such as optical aberration and geometry parameters of cornea, lens, retina, fovea and sclera) at that earlier age and desired original state. From that OOC estimate then TOC can be calculated or estimated assuming most likely changes in eye properties over the time interval between the time for which OOC was estimated and time of the expected corrective procedure. The calculation or estimation of various parameters leading to TOC can be performed using scientific and clinical data on development of relevant eye features and properties with time, as they are known to the ophthalmic science or will become available by the time of the procedure.

After a TOC is determined, the refractive change of the patient's eye (e.g., defocus, aberrations) required to achieve the optical configuration best corresponding to TOC for that individual may be determined That refractive change can be achieved in many ways, e.g. by any refractive change of cornea or any natural or artificial lens in the eye, or by replacing fully or partially cornea or the lens (natural or artificial), or by any combination thereof.

The selected refractive change may be implemented to achieve the TOC by any suitable methods and devices known in the art. As mentioned above, various methods and devices for decreasing aberrations of the eye are known in the art. See, e.g., US Patent Application Publication Nos. 20020105617, 20070093891, 20040088050, 20070121064, 20070258044, 20090036980, 20110082542, 20120059463, 20080039825, 20090210054 and 20130060330; and U.S. Pat. Nos. 8,287,593, and 7,585,075. Each of these documents is incorporated herein by reference.

In one example, the TOC can be achieved by refractive changes in cornea by changing its shape and/or refractive index by methods and devices that are known per se to those skilled in the art, such as LASIK, PRK, corneal crosslinking, laser-induced changes of corneal refractive index, change of corneal shape by implantation of solid elements (e.g., INTACTS); by refractive changes to the crystalline lens, such as of laser lensectomy. Alternatively, TOC can be achieved by adding lenses onto or into cornea, into the anterior chamber of the eye, into the posterior eye chamber between iris and natural lens, or by replacing the natural lens for an artificial IOL. Refractive change can be achieved by many methods known in the art.

Another preferred device for achieving the TOC is a hydrogel implant into the eye which refractive index can be changed by absorption of electromagnetic energy. The same end can be achieved by changing refractive index of the natural crystalline lens of cornea by absorption of electromagnetic energy. As described above, change of the optical properties of the natural (e.g., human cornea) or an artificial lens by changing refractive index of their material is known in that art. See, e.g., U.S. Pat. Nos. 6,102,906, 8,292,952, 8,920,690, 9,192,292, 9,023,257, 9,186,242, 9,107,746; 8,901,190, 8,932,352, 8,337,553, 7,789,910, 8,486,055, 8,512,320, and 8,617,147; and US Patent Application Publication Nos. 20160074967, 20130268072, 20090287306, 20130138093, 20130178934, 20100298933, 20080001320, 20090143858; 20090143858, 20110071509, 20130226162, 20140107632, and 20120310223. Each of these documents is incorporated herein by reference.

Spherical aberration can be changed by implantation of an aspheric lens with conic optical surfaces using methods known in the art. See, e.g., WO2014111769, U.S. Pat. Nos. 4,846,832, 5,674,283, 4,994,083, 4,955,903, 7,192,444, 6,007,747, 7,350,916, 8,167,940, 8,668,333, 8,409,481; and US Patent Application No. 2006022728. Each of these documents is incorporated herein by reference.

Either optical aberrations of the cornea or the implanted artificial lens can be adjusted in order to decrease the overall aberration of the eye. This is usually achieved by introducing a controlled degree of asphericity that also, in addition to causing certain amount of SA, also increases the depth of focus of the lens. Such methods and devices are described in numerous patents and patent applications. See, e.g., US Patent Application Publication Nos. 20130072591, 20010027314, 20020138069, 20020138070, 20030093066, and U.S. Pat. Nos. 7,637,947 and 8,154,804. Each of these documents is incorporated herein by reference.

Some have described intraocular lenses that change optical properties by transfer of fluid within its optics, and can be potentially used even for adjustment of SA, although that goal is usually not explicitly stated. See e.g., US Patent Applications Publication Nos. 20040184158, 20060061729, 20070299487, 20130060331, 20090281620, 20140257478, and 20140257479; and U.S. Pat. Nos. 8,048,155, 7,264,351, 7,278,739, 7,438,723, 7,485,144, 8,715,345, 7,601,169, 8,500,806, and 8,167,941. Each of these documents is incorporated herein by reference.

The resulting lens and/or cornea may not necessarily be optically perfect in the usual sense of that term by themselves or in their combination, on the contrary, they should be optically imperfect in their combination to approximate optical aberrations of the young eye of that particular patient.

In the case that the corrective procedure aimed to achieve TOC involves an exchange of the crystalline lens for an artificial lens, than that artificial lens could be custom-made or custom-adjusted IOL for that particular patient, and preferably custom-made or custom-adjusted Bioanalogic IOL according to Stoy, V. et al, Bioanalogic Intraocular Lens, U.S. Patent Application Publication No. 20150351901, which is incorporated by reference in its entirety, or IOLs described in any of the following US Patents: Wichterle, O., Soft And Elastic Intracameral Lens And Method For Manufacturing Thereof, U.S. Pat. No. 4,846,832; Stoy, V., Implantable Ophthalmic Lens, A Method Of Manufacturing Same And A Mold For Carrying Out Said Method, U.S. Pat. No. 5,674,283; and Michalek, J. et al, Method Of Manufacturing An Implantable Intraocular Planar/Convex, Biconvex, Planar/Concave Or Convex/Concave Lens And A Lens Made Using This Method, U.S. Pat. No. 8,409,481. Each of these documents is incorporated by reference in its entirety.

The optical surfaces of such lenses are described as conical surfaces, or as a surface formed by a combination of two or more conical surfaces. Conic curve may be e.g. parabola, ellipse or circle. In one embodiment, the shape is hyperbole since lenses with hyperboloid surfaces have negative spherical aberration that conforms best to the optical properties of a young human lens. Conic curves are defined by two constants—central radius of curvature Ro in the apex of the curve, and the conic constant k. The conic constant value defines the basic character of the conic curve. For instance, hyperbole is defined by the negative value of the conic constant k.

Another advantageous type of curve is one of the curves defined by a function $k(r)$ where r is the distance from the axis of symmetry and at the center (apex) at $r=0$ is $k(0)=k$. This type of curve is called "aconic" since it is not a true conic curve, although it may approximate some of its properties. In one example, $k(r)$ is a monotone function of r in the interval used for our optical design. In another example, its first derivative according to r is negative in that interval. The aconic function suitable for our optical purpose can be expressed in various ways, for instance as a polynomial. In addition to the aconic function $k(r)$, the apex radius Ro can also be a function of distance from the axis of symmetry r. Then $R=R(r)$ and achieves value $Ro=R(0)$ at the center of the lens where $r=0$. The function $R(r)$ is may be a monotonous function of r and its derivative by r is may be positive. In the case that $R(r)$ is not a constant, then $k(r)$ may be a constant, and vice versa.

The use of optical surfaces created by rotation of the aconic curve (such as aconic hyperbole) allows the creation of smooth optical surfaces without any disturbing transitions or discontinuities that fit into geometry constrains of the bioanalogic IOL design. Such customized lens can be designed to achieve the desirable TOC parameters.

Alternatively, an un-customized IOL could be implanted, and then the eye optics could be customized by customization of the corneal optics achieved either by controlled corneal ablation (LASIK) or by a controlled change of corneal refractive index using femtosecond laser (IRIS), or controlled corneal cross-lining or perhaps by another method of corneal optics customization known at the time of the procedure.

Alternatively, customization of the optics of an already implanted lens can be achieved in situ by, e.g., using a femtosecond laser ablation, or by femtosecond laser induced change of refractive index or its gradient (GRIN), or by photopolymerization of components of so called Calhoun intraocular lens.

Advantageously, the custom-made or custom modified IOL is an IOL with extended field of focus or accommodating IOL.

In addition to the above mentioned methods of in situ postoperative adjustment of optical parameters (e.g., photo-crosslinking or photopolymerization, laser ablation, photo-adjustment of refractive index, etc.) an alternative method is changing refractive interface by activation of shape transition of memory elements embedded in the optics by heating at least part of them locally above the pre-set transition temperature that is higher than body temperature.

Memory elements can be made of memory polymer or memory alloy elements or both. An advantage of the memory polymer elements is that they can retain any shape at body temperature between two or even three pre-defined shapes, they have lower density, they can be transparent, and they can be deformed with higher strain. Significantly, the optical zone can be made partly of fully from a transparent memory polymer having transition temperature slightly above the highest possible body temperature, and change the shape of the optics by heating selected part(s) of the memory polymer above its transition temperature.

The transition of memory elements between their "stable" states is carried out by typically by local heating of the memory material above its transition temperature. The can be achieved by absorption of electromagnetic radiation, by electric induction, by ultrasound absorption, etc. The heating has to be precisely localized and carefully controlled in order to avoid damage to surrounding tissues.

Reshaping of the optics can be achieved by the circular element with alternating stretching and contracting segments. By activating selected segments we can either change spherical refractive power or astigmatism or both.

The memory elements can be the metal alloy memory elements, such as memory elements located in haptics of an implantable lens described in US Patent Application Publication No. 20140094908, incorporated by reference in its entirety, or can be at least partly include memory polymers such as are described by Stoy, V. in U.S. Pat. No. 4,731,079, Sulc, J. et al in U.S. Pat. No. 4,946,470, Kahook Malik et al in US Patent Application Publication No. 20120232648 and 20120232651, Balbierz, D. J. et al., in U.S. Pat. No. 5,964,744 and A. Phillips in the U.S. Pat. No. 8,998,984. All of these documents are hereby incorporated by reference in its entirety. It is understood that some of these references primarily describe shape memory polymers with transition temperature lower than eye temperature, but those skilled in the art can readily change composition of such materials to have transition temperature above the eye temperature.

The lens re-shapeable by the shape-memory effects can be implanted anywhere along the optical path, e.g. into the cornea, into the anterior chamber or onto the posterior chamber either supplementing or replacing the natural lens.

As used herein the term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4 and "17%" may mean 16.5% to 17.4%.

Example

An example artificial lens shaped according to the above methods may be a hydrogel device implantable into the posterior chamber of human eye for replacement of the natural crystalline lens.

The features contributing to the overall function and combined according this disclosure include size and shape of the implant; material properties; surface properties; optical properties; implantation method; and manufacturing method. We will describe the various features below and provide exemplary configurations of how individual features mutually interact to provide beneficial effect. It is important to recognize that the implant may combine several of the described features to achieve desirable effects, however, the embodiments of the present invention is not limited to the exemplary configurations described below.

Figure 4A:
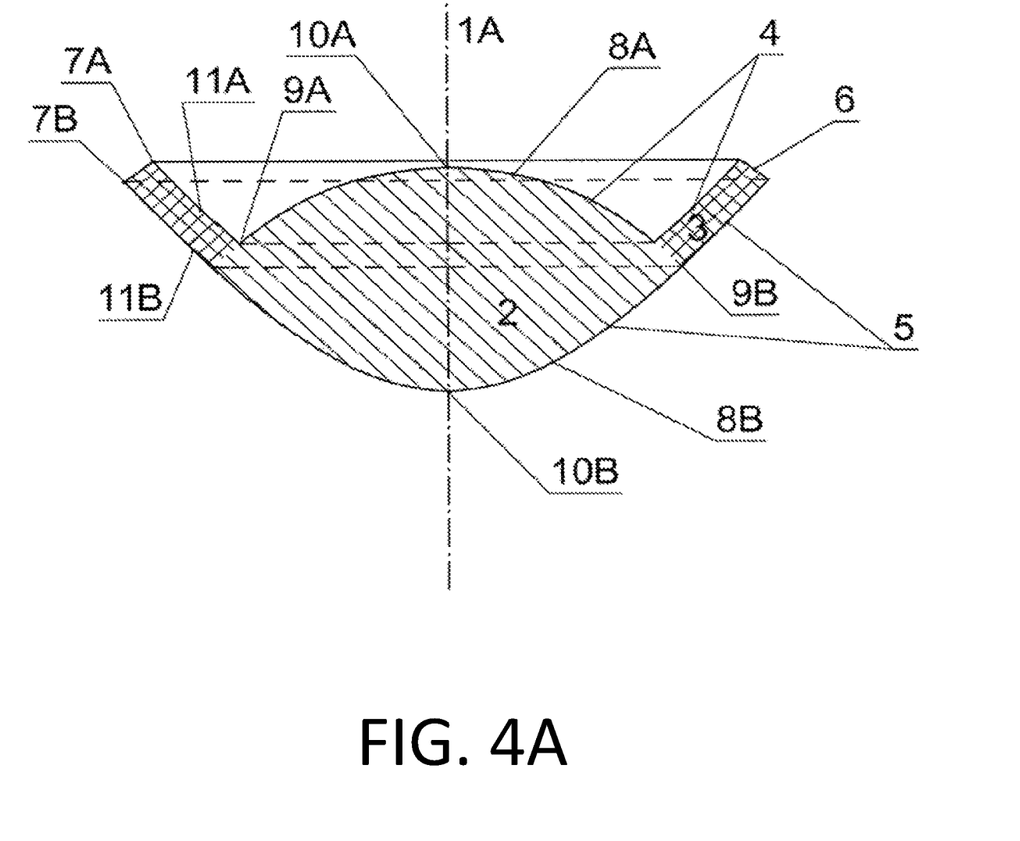
FIG. 4A is a cross-sectional view of a bioanalogic intraocular lens according to an exemplary embodiment of the invention.
Figure 4B:
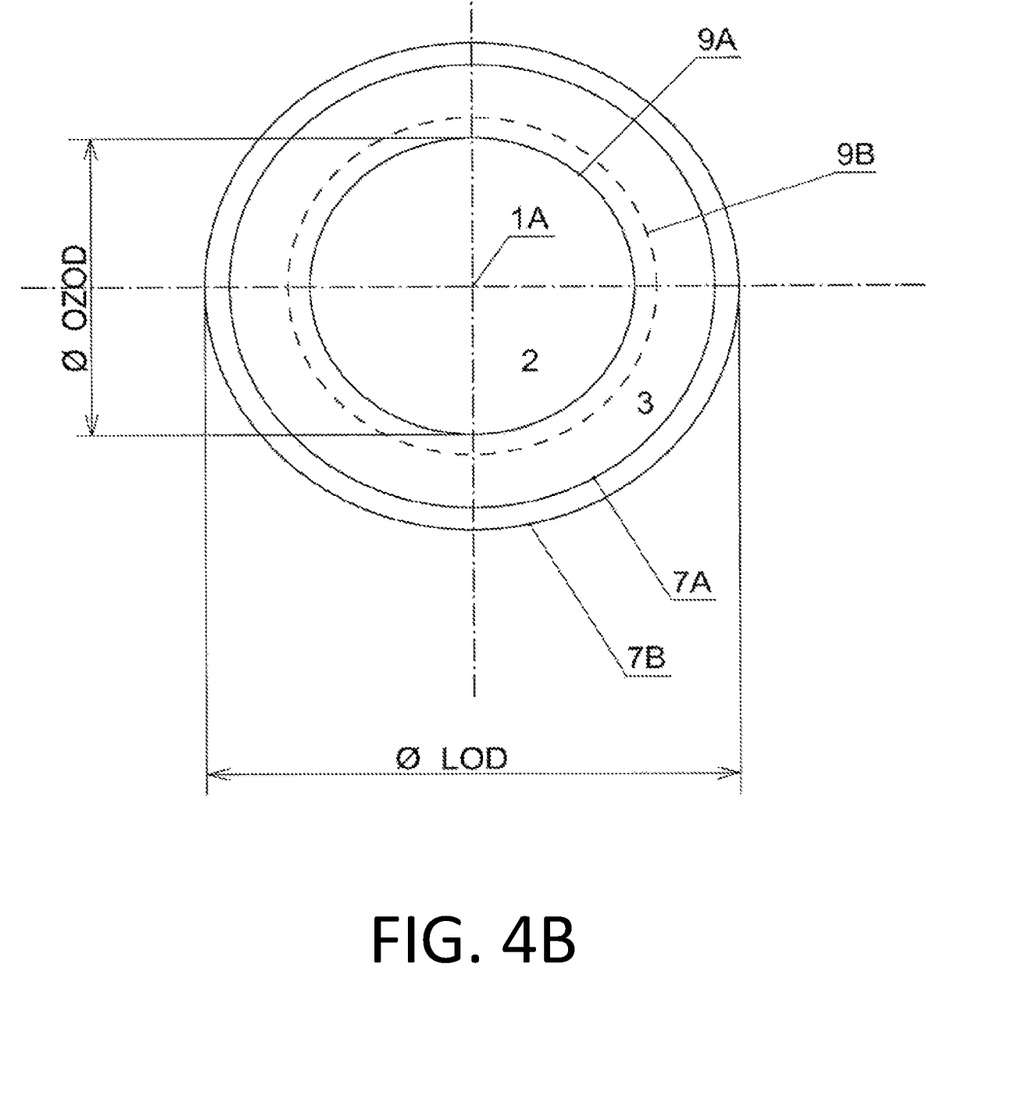
FIG. 4B is a top view of the lens of FIG. 4A.

Referring to FIGS. 4A and 4B, the implant has a main optical axis 1A with a central optical part 2 and a peripheral supporting part 3. The overall shape of the implant is defined by its anterior surface 4, posterior surface 5 and the transition surface 6 between the upper boundaries 7A and 7B of the anterior and posterior faces, respectively. Each face is composed of two or more surfaces. The anterior central optical surface 8A has boundary 9A and central posterior optical surface 8B has boundary 9B. Each of the surfaces may be divided into two or more zones with the boundary between them being circles, straight lines or otherwise defined shapes. The apexes of the central anterior optical surface 10A and central posterior optical surface 10B are positioned on the main optical axis 1A. The anterior peripheral supporting surface is 11A and the posterior peripheral supporting surface is 11B.

The boundaries 7A and 7B are distinguishable as a discontinuity on the top of the anterior and posterior surfaces 4 and 5, respectively. Such a discontinuity lay in the inflexion point of the surface in the direction of the optical axis, or a in a point of discontinuity of the second derivative of the surface in the direction of the optical axis. The boundary can be rounded and continuous, but advantageously it is formed by a sharp rim or edge. The advantage of the sharp edge is in forming the obstacle to migration of cells such as fibroblasts along the capsule surface (the usual reason for posterior capsule opacification).

The overall lens diameter is defined as the larger diameter of the boundaries 7A and 7B. The lens optical zone diameter is defined as the smallest diameter of the boundaries 9A and 9B. The posterior sagittal depth is the vertical distance between the posterior apex 10B and the plane defining the posterior boundary 7B. Central thickness is the distance between apexes 10A and 10B. Anterior depth is the vertical distance between the anterior apex 10A and the plane defining the anterior boundary 7A.

The implantable lens in this example is made of a hydrogel with water content between 40 to 50%-wt. of liquid in equilibrium with intraocular environment, and preferably between 41% and 45%/wt. The hydrogel contains fixed negative charge (FNC) due to the pendant carboxylic groups in the polymer component of the gel. The hydrogel contains a minor component of units with UV-absorbing pendant groups, such as derivatives of benzophenone or benztriazole. The corresponding refractive index approximates the effective refractive index of NCL having values between about 1.41 and 1.44 at wavelength about 630 nm. Hydrogels of these properties possess high biocompatibility and excellent optical stability.

Figure 5A:
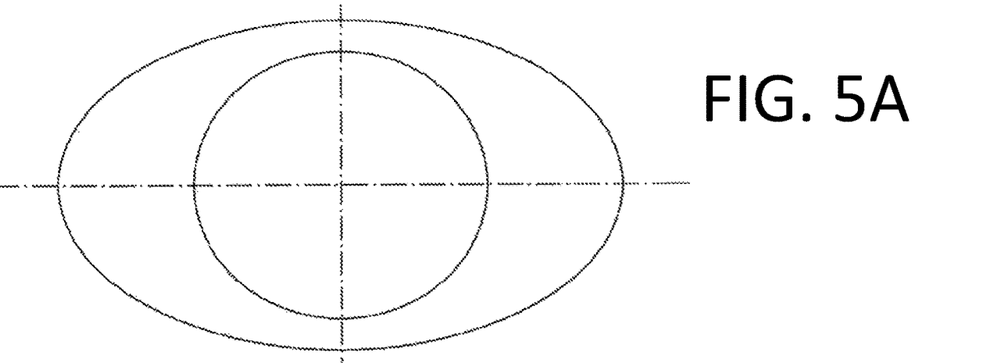
FIG. 5A is a top view of another exemplary embodiment of a lens with a circular optical part and elliptical support part.
Figure 5B:
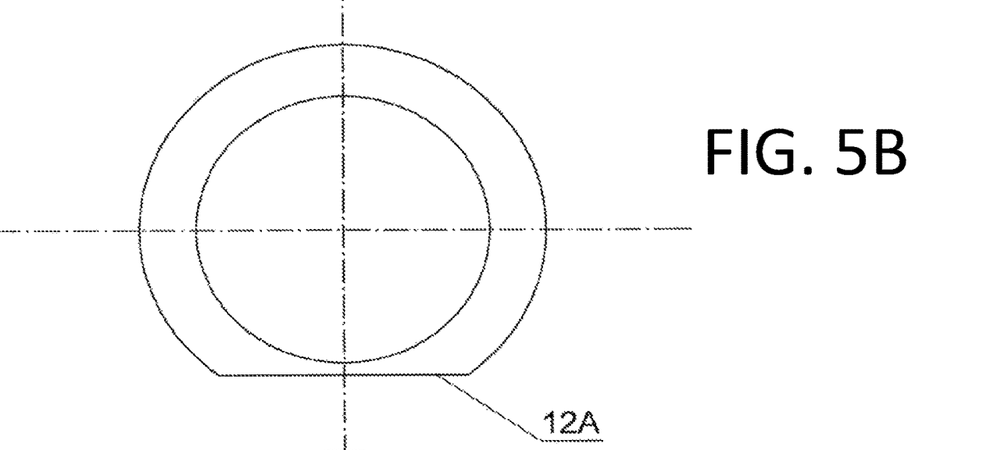
FIG. 5B is a top view of another exemplary embodiment of a lens with a circular support part truncated by a single straight cut.
Figure 5C:
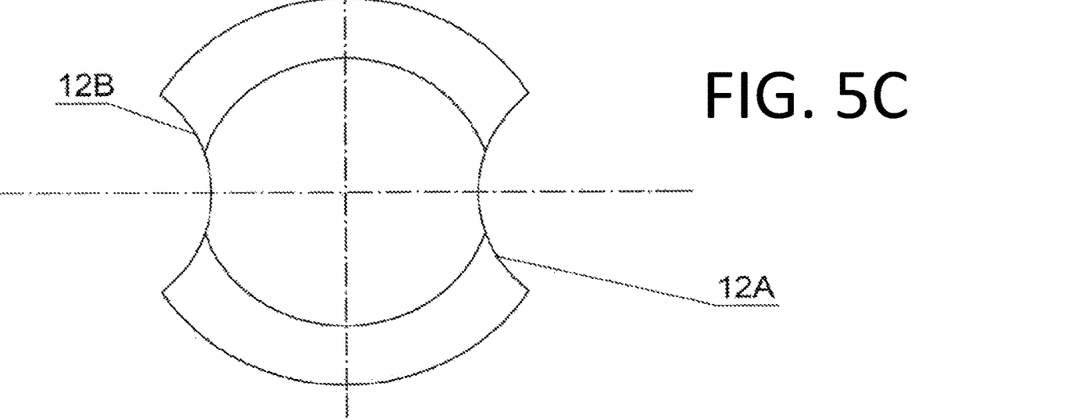
FIG. 5C is a top view of another exemplary embodiment of a lens with a circular support part truncated by two symmetric crescent cuts.
Figure 5D:
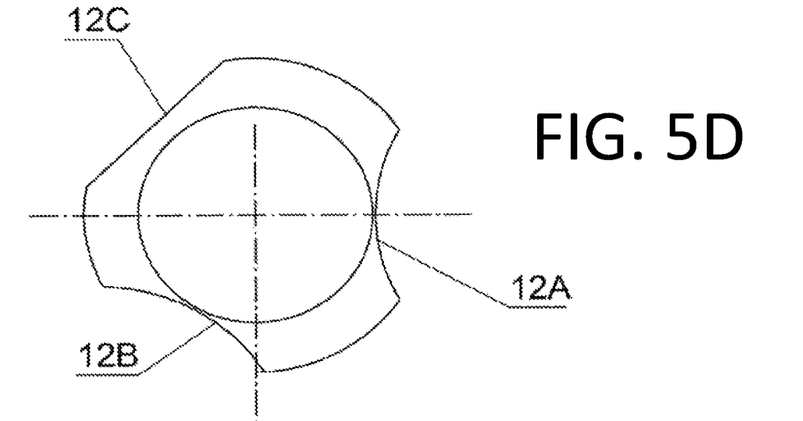
FIG. 5D is a top view of another exemplary embodiment of a lens with a circular support part truncated by one straight and two crescent cuts.
Figure 5E:
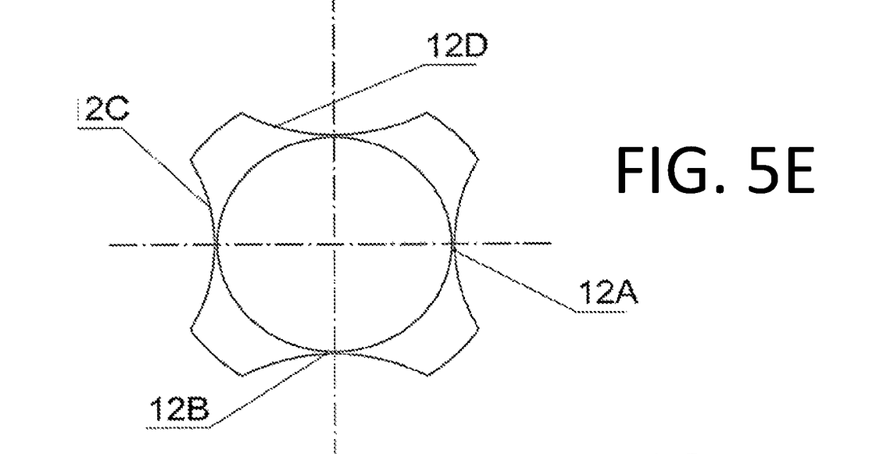
FIG. 5E is a top view of another exemplary embodiment of a lens with a circular support part truncated by four symmetric crescent cuts.

The main optical axis 1A may be the axis of symmetry in the case that boundaries 7A and 7B, as well as boundaries 9A and 9B, are defined by circles in the plane perpendicular to the optical axis, and if the central optical part 2 is symmetrical and e.g., does not have any cylindrical component. Such implant with symmetric circular footprint is shown in FIG. 4B. However, the rims and boundaries may have other than circular footprint, e.g. elliptical as shown in FIG. 5A, or may have the footprint shaped as a truncated circle in FIGS. 5B to 5E with single, double, triple or quadruple truncating cuts 12A to 12D. These truncated footprint shapes serve several purposes:

They provide better access into the space behind the lens during the implantation. It is important to clean this space well in order to remove any viscoelastic polymers or lubricants or other auxiliary agents before the surgical incision is closed.

They prevent rotation of the lens after the capsule shrinks around the IOL. This is particularly important for toric lenses.

They facilitate folding and insertion through a small incision.

Figure 5F:
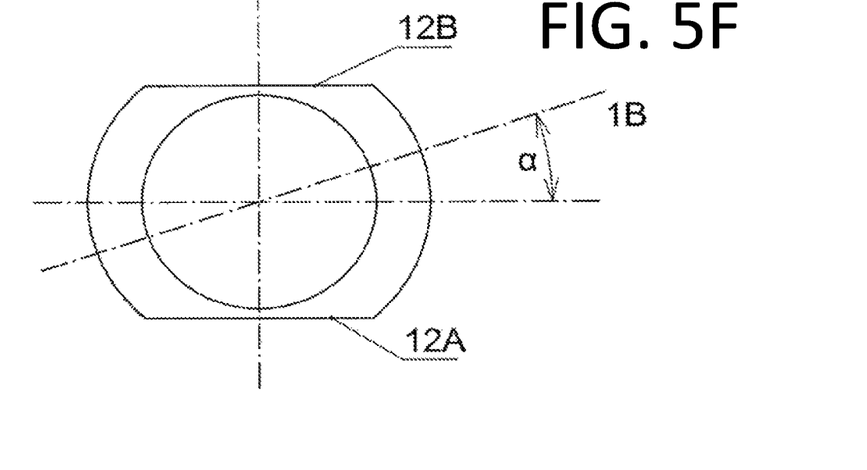
FIG. 5F is a top view of another exemplary embodiment of a lens with a circular support part truncated by two straight parallel cuts and the cylindrical lens with cylinder axis 1B in the angle α with regard to the cuts direction.

In the case that the optics has a cylindrical component, then the cylinder axis 1B will be positioned in a defined way with respect to the asymmetry of the outside rim, e.g. be in the angle α to the truncating cuts 12A and 12B as shown in the FIG. 5F. Needless to say that the truncating cuts 12A to 12D may not be necessarily straight cuts, but may be suitably formed to e.g. a crescent shape, and their number may be even higher than 4. Also, the truncating cuts may not be of the same length or positioned symmetrically. It can be appreciated that the footprint with truncated rim will facilitate folding of the implant and its insertion through a small surgical incision. In addition, the asymmetric rim footprint will prevent the implant rotation once the capsule settles around it. This is particularly important for toric lenses with a cylindrical component designed to compensate for astigmatism.

The posterior surface 5 is shaped and sized to approximate the shape and size of the posterior surface of the natural lens and to achieve contact with at least the major part of the posterior capsule of the eye. This is important for several reasons:

The implant will keep the posterior capsule in its natural shape, unwrinkled and smooth for the optimum optical performance;

The tight contact between the capsule and the implant will prevent migration of fibroblasts that could cause the posterior capsule opacification; this is particularly effective if the posterior surface is highly hydrated and carrying fixed negative charge.

The implant will occupy the space vacated by the posterior side of the natural lens and keep thus vitreous body from advancing forward and prevent thus the decrease of the pressure of vitreous body against retina (which could facilitate retinal detachment and/or cystoic macular edema).

It should be noted that the intimate contact between the implant and posterior capsule is beneficial particularly if the contacting surface of the implant is hydrophilic and carrying fixed negative charge in order to prevent capsular fibrosis and its consequent stiffening, opacification and contraction that would interfere with the implant function (or could even dislocate it), as will be described hereinafter.

In the preferred embodiment of the invention, at least the major part of the posterior surface 5 is formed by a generally smooth convex surface formed by rotation of conic sections or aconic curves around the optical axis, or a combination of such surfaces. The peripheral part is preferably formed by a conic surface or a hyperboloid-like aconic surface, while the central optical surface is preferably hyperboloid, paraboloid or spherical surface (or a combination thereof). The sagittal depth of the posterior surface (i.e. the vertical distance between the posterior central optical surface apex 10B and the boundary of the posterior surface 7B, measured on the main optical axis 1A) should be larger than 1.1 mm in order for lens to perform its function well. To perform well in the whole refractive range, the posterior sagittal depth should be larger than 1.25 mm, advantageously larger than 1.75 mm and preferably larger than 2 mm, but in any case less than about 2.75 mm.

The overall outer diameter of the implant (LOD) is important for its centricity, position stability and capsule-filling capability. The outer diameter of the posterior surface 5, i.e. the largest dimension of the posterior outer boundary 7B (in the plane perpendicular to the main axis 1A) should be larger than 8.4 mm, desirably at least 8.9 mm and preferably at least 9.2 mm. The largest outer diameter permissible is about 11 mm, but desirably should be lower than 10.75 mm and preferably at smaller than 10.5 mm The considerable flexibility in the outer dimensions is allowed by several factors—flexibility of the lens, and particularly flexibility of the outer peripheral supporting part 3 that can accommodate various capsule sizes and capsule contraction without deforming the central optical part 2.

In at least one embodiment, the lens according to this disclosure is manufactured by solidification of liquid polymer precursors. In the preferred embodiment, the solidification takes place in contact with a solid mold, particularly a mold made of a hydrophobic plastic. It can be appreciated that the surface microstructure of a polymer depends on the environment in which its solidification took place. The surface microstructure will be different if the solidification occurs on the solid liquid interface that if it takes place on the liquid-liquid or liquid-gas interface. Preferably, at least all optical surfaces are created by solidification of the precursor on a solid interface. Even more preferably, whole surface of the implant is formed by solidification of a liquid precursor against a solid surface, particularly a hydrophobic plastic surface. Preferred plastic for the mold is a polyolefin, and particularly preferred plastic is polypropylene. The polyolefin has low polarity and has low interaction with highly polar monomers that are used as hydrogel precursors. Likewise, the hydrogel formed by the liquid precursor solidification has very low adhesion to the mold surface and can be cleanly detached without even a microscopic surface damage. This is important for both optical properties and for long-term biocompatibility of the implant.

Manufacturing a relatively large lens of a precise shape by molding is difficult. It is recognized by those skilled in the art that any solidification of the liquid precursor is accompanied by the volume shrinkage that may even exceed 20 percent. In a closed mold of a constant volume, such shrinkage will prevent copying of the internal mold surface and cause formation of vacuoles, bubbles, surface deformities and other imperfections. This is the main reason why the meniscus casting methods described above were used for IOL molding. Other inventors have described a method and a mold design allowing the excess of monomers to be transported from adjacent spaces by the suction created by the volume contraction (Shepherd T., U.S. Pat. No. 4,815,690, incorporated herein in its entirety). However, this method cannot be used in cases where the liquid precursor gellifies at a low conversion (e.g., 5 to 10 percent) due to the crosslinking polymerization. In that case one can use the method described in the International Publication Number WO 2014/111769 A1 and, as an example, the mold which is shown in FIG. 8 of that reference that is incorporated herein in its entirety.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A method of optimizing vision in an eye of a patient comprising the steps of:
   determining a target optical configuration for the patient's eye;
   determining the refractive change of the patient's eye required to achieve the target optical configuration; and
   implementing the determined refractive change to achieve the target optical configuration,
   wherein the target optical configuration is determined by performing a thorough eye examination of the patient's eye, and extrapolating relevant optical parameters back to the time when the eyesight of that patient was satisfactory, and calculating or estimating the values of relevant optical parameters at that earlier age, the relevant optical parameters including one or more of aberrations, refractive indices, and geometry of ocular structures,
   wherein the implementing step comprises selecting an intraocular lens (IOL) implantable into the patient's eye,
   wherein the intraocular lens comprises a hydrogel, and comprises:

a body defining a central optical part and an integral peripheral supporting part, both of which extend about a main optical axis, wherein the central optical part has a refractive power;

the central optical part having a central anterior optical surface within a first boundary and defining an anterior apex, and a central posterior optical surface within a second boundary and defining a posterior apex, wherein the central anterior optical surface has a refractive power, and wherein the central posterior optical surface has a refractive power;

the peripheral supporting part having an anterior peripheral supporting surface extending from the first boundary such that the central anterior optical surface and the anterior peripheral supporting surface define an anterior surface with a first upper boundary, and a posterior peripheral supporting surface extending from the secondary boundary such that the central posterior optical surface and the posterior peripheral supporting surface define a posterior surface with a second upper boundary, and wherein the first upper boundary is anterior to the anterior apex of the central anterior optical surface;

a transition surface extending between the first upper boundary and the second upper boundary;

wherein the central anterior optical surface and the central posterior optical surface are defined by rotation of one or more conic sections along the main optical axis; and;

wherein at least the central posterior optical surface is a hyperboloid surface, wherein the intraocular lens is adjustable postoperatively, and the implementing step further comprises a postoperative adjustment of the intraocular lens, wherein the postoperative adjustment is achieved by a controlled absorption of electromagnetic radiation, and wherein the electromagnetic radiation adjustably changes the refractive index of selected volume elements of the intraocular lens, or adjustably changes the geometry of selected shape memory elements embedded in the intraocular lens due to heating of said selected shape memory elements above their transition temperatures.

2. The method according to claim 1, wherein the thorough eye examination of the patient includes determining geometry of the macula.

3. The method according to claim 1, wherein the intraocular lens has spherical aberration customized to achieve the target optical configuration of the eye.

4. The method according to claim 1, wherein the hydrogel comprises a liquid content higher than 17% by weight in equilibrium with intraocular environment, or between 40% and 50% by weight in equilibrium with intraocular environment.

5. The method according to claim 1, wherein the hydrogel comprises a polymer containing monomer units with pendant carboxylic group.

6. The method according to claim 1, wherein the hydrogel comprises a polymer containing monomer units with pendant groups capable of absorption of UV radiation.

7. The method according to claim 1, wherein the hyperboloid surfaces is an aconic hyperboloid surface.

* * * * *